United States Patent [19]

Addor et al.

[11] Patent Number: 4,575,560

[45] Date of Patent: Mar. 11, 1986

[54] INSECTICIDAL DIAMINOGUANIDINE HYDRAZONE COMPOUNDS

[75] Inventors: Roger W. Addor; Donald P. Wright, Jr., both of Pennington; Jack K. Siddens, Princeton Junction; John J. Hand, Lawrenceville, all of N.J.

[73] Assignee: American Cyanamid Company, Stamford, Conn.

[21] Appl. No.: 704,974

[22] Filed: Feb. 25, 1985

[51] Int. Cl.$^4$ .............. C07C 125/065; C07C 149/40; C07C 133/10; C07C 109/10; C07D 295/16; C07D 319/16; C07D 317/48

[52] U.S. Cl. ........................................ 560/27; 560/9; 564/149; 564/150; 564/228; 546/197; 546/226; 548/526; 548/538; 549/377; 549/378; 549/380; 549/448; 549/451; 549/452; 514/452; 514/465; 514/482; 514/590; 514/632

[58] Field of Search ............... 564/228, 149; 548/526, 548/538; 546/197, 226; 549/377, 378, 380, 448, 451, 452; 560/9, 27

[56] References Cited

U.S. PATENT DOCUMENTS 3,992,446 11/1976 Tomcufcik ..................... 564/228

FOREIGN PATENT DOCUMENTS 824811 7/1975 Belgium .

*Primary Examiner*—Natalie Trousof
*Assistant Examiner*—L. Hendriksen
*Attorney, Agent, or Firm*—Alice C. Brennan

[57] ABSTRACT

The invention is insecticidal diaminoguanidine hydrazone compounds which are also effective antifeeding agents for insects and methods for their preparation.

7 Claims, No Drawings

INSECTICIDAL DIAMINOGUANIDINE HYDRAZONE COMPOUNDS

The invention is diaminoguanidine hydrazone compounds of the formula (I)

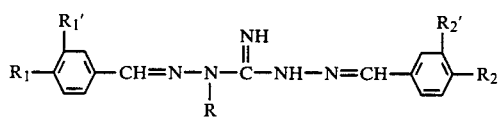

wherein $R_1'$ and $R_2'$ are H, and $R_1$ and $R_2$ are individually selected from fluoro, chloro, bromo, trifluoromethyl, $CF_3CH_2O$, $CHF_2X$, $CF_3X$, $CHY_2CF_2X$, or $CHFYCF_2X$, where X is O or S and Y is F or Cl; or $R_1$ and $R_1'$ or $R_2$ and $R_2'$ are $-OCF_2O-$, $OCF_2CHFO-$, $-OC(CH_3)_2-O-$ or $-OCF_2CF_2O-$;
R is H,

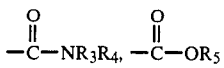

where $R_3$ is $C_1$-$C_2$ alkyl, or $C_1$-$C_2$ haloalkyl, $R_4$ is hydrogen or $C_1$-$C_2$ alkyl; or $R_3$ and $R_4$ when taken together may form a ring represented by $CH_2(CH_2)_n-$ where n is 3 or 4; $R_5$ is $C_1$-$C_4$ alkyl optionally substituted with one to three halogens or $C_3$-$C_4$ alkenyl, with the proviso that when R is

$R_1$ and $R_2$ are $CF_3CH_2O$, $CHF_2X$, $CF_3X$, $CHY_2CF_2X$, or $CHFYCF_2S$, where X is O or S and Y is F or Cl; $R_1$ and $R_1'$ or $R_2$ and $R_2'$ are $-OCF_2O-$, $-OC(CH_3)_2-O-$, $OCF_2CHFO$ or $-OCF_2CF_2O-$.

While the use of diaminoguanidine compounds as antiprotozoal agents and especially as anticoccidial agents is known in the art as described in U.S. Pat. No. 3,992,446 and Belgian Pat. No. 824,811, there is no suggestion in the literature that diaminoguanidine hydrazone compounds are effective insecticidal agents or further that some of these compounds exhibit antifeeding activity when applied to plants.

The diaminoguanidine hydrazone compounds of the invention as well as other diaminoguanidine hydrazone compounds are effective in controlling lepidopterous insects and are useful for protecting agronomic crops, trees, shrubs, and ornamentals from attack by these insects. Many of these compounds also exhibit antifeeding activity thus providing additional protection to treated plants.

Novel formula (Ia) diaminoguanidine dialkyl ureas of the invention wherein R is

in formula (I) may be readily prepared by the reaction of an appropriately substituted diaminoguanidine of formula (Ib) wherein R is H in formula (I) with from 1 to 2 molar equivalents of N,N-disubstituted carbamoyl chlorides of formula (III) in a solvent such as acetonitrile in the presence of a tertiary amine such as triethylamine or diisopropylethylamine as illustrated in Flow Diagram I below.

FLOW DIAGRAM I

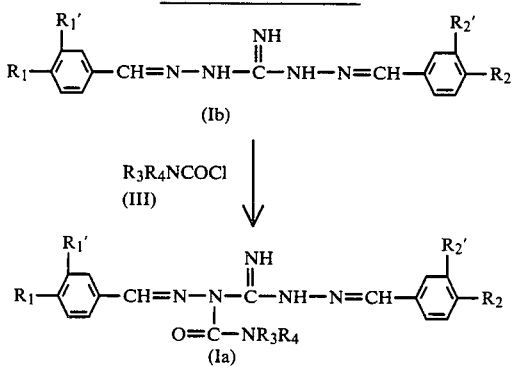

wherein $R_1$, $R_1'$, $R_2$, $R_2'$, $R_3$ and $R_4$ are as described above.

Formula (Ia) diaminoguanidine monosubstituted ureas may be prepared by the reaction of the appropriately substituted formula (Ib) diaminoguanidine with from 1 to 1.5 molar equivalents of a formula (IV) isocyanate in an inert solvent such as ether as illustrated in Flow Diagram II below.

FLOW DIAGRAM II

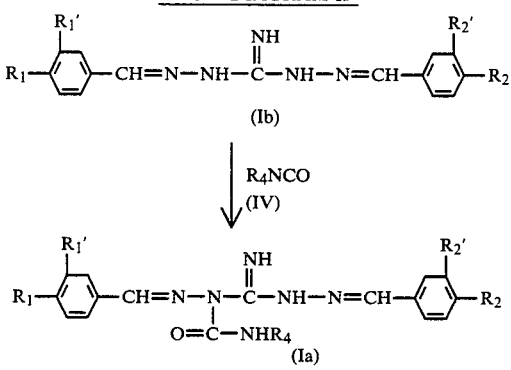

wherein $R_1$, $R_1'$, $R_2$, $R_2'$ and $R_4$ are as described above.

When $R_1$ and $R_2$ and $R_1$, $R_1'$ and $R_2$, $R_2'$ are not the same, both of the above reaction sequences give rise to isomeric mixtures of the formula (Ia) products as indicated below.

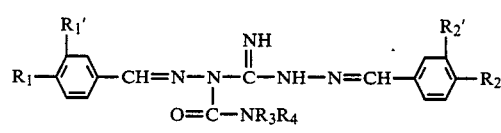

and

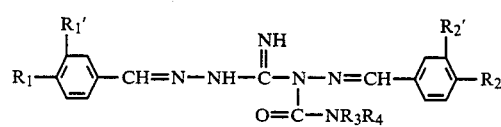

wherein $R_1$, $R_1'$, $R_2$, $R_2'$, $R_3$, and $R_4$ are as described above.

Diaminoguanidine hydrazones of formula (Ib) may be prepared by the reaction of two molar equivalents of an appropriately substituted aldehyde of formula (Va) dissolved in an organic solvent with an alcoholic or aqueous alcoholic solution of a diaminoguanidine salt of the formula

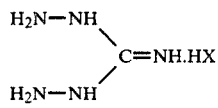

as illustrated in Flow Diagram III(a) below.

Uniquely, unsymetrical diaminoguanidines where $R_1 \neq R_2$ and $R_1$, $R_1' \neq R_2$, $R_2'$ may then be obtained cleanly by the novel reaction of a symetrical diaminoguanidine with a minimum of one molar equivalent of hydroxylamine hydrochloride followed by reaction of the thus-formed monosubstituted guanidine with an appropriately substituted aldehyde of formula (Vb) as illustrated in Flow Diagram III(b) below.

FLOW DIAGRAM III

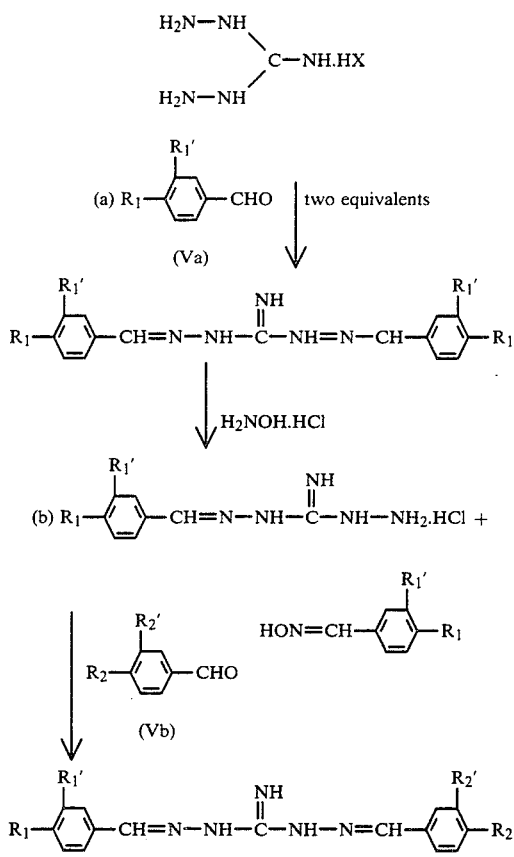

The Formula (Ib) insecticidal diaminoguanidines may also be converted to insecticidal Formula (Ic) diaminoguanidines by reaction of with 1.0 to 1.25 molar equivalents of an appropriately substituted chloroformate of formula (VI) in an organic solvent such as acetonitrile, ether, toluene, methylene chloride and the like, in the presence of a tertiary amine such as triethylamine or diisopropylethylamine as illustrated in Flow Diagram (IV) below.

FLOW DIAGRAM IV

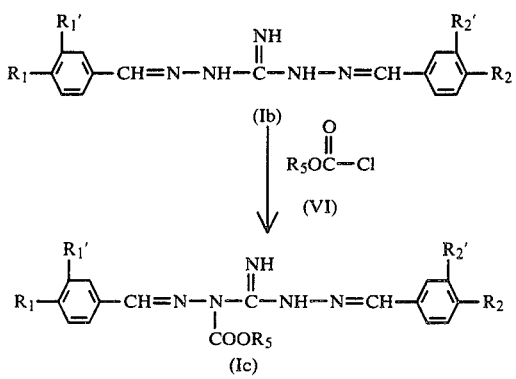

wherein $R_1$, $R_1'$, $R_2$, $R_2'$ and $R_5$ are as described above.

The present invention is further illustrated by the following non-limiting examples.

EXAMPLE 1

Preparation of p-(2,2,2-trifluoroethoxy)benzaldehyde

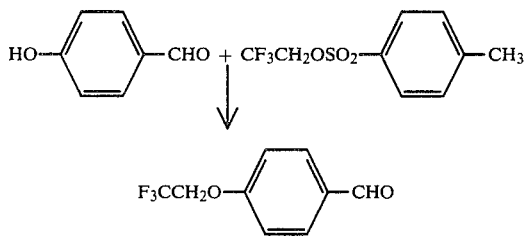

Potassium hydroxide pellets (85%, 13.2 g, 0.2 mol) are added to 4-hydroxybenzaldehyde (24.4 g, 0.2 mol) and 18-crown-6 (2.6 g, 5% mol) in diglyme (150 mL). The red reaction mixture is stirred for 16 hours at room temperature and then a solution of 2,2,2-trifluoroethyl-p-toluenesulfonate (50.8 g, 0.2 mol) in diglyme (100 mL) is added over 30 minutes, after which the mixture is allowed to stir at room temperature for 45 minutes. The resulting suspension is then heated at reflux for 24 hours. The mixture is cooled to 10° C. and poured into ice water (1300 mL). The organic materials are extracted with ether (4×200 mL), and the extracts washed with 5% sodium hydroxide (2×100 mL), water (2×100 mL) and saturated sodium chloride (1×100 mL), and dried over MgSO$_4$. Evaporation of the ether gives an amber oil which is purified by high performance liquid chromatography using silica gel on a Waters 500 unit and 50:50 hexane and methylene chloride as eluant to give 12.3 g of the title product with R$_f$ 0.25. Anal. Calcd for C$_9$H$_7$F$_3$O$_2$ (204.15) C, 52.94; H, 3.43. Found C, 52.04; H, 3.59.

EXAMPLE 2

Preparation of 1,3-bis{[p-(tetrafluoroethoxy)benzylidene]-amino} guanidine

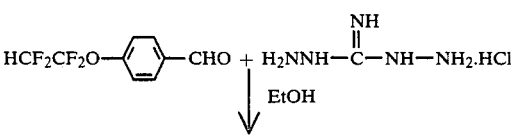

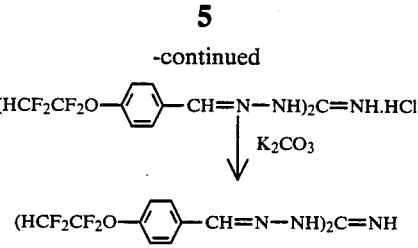

A solution of p-tetrafluoroethoxybenzaldehyde (35.07 g, 0.158 mol) in 2B alcohol (20 mL) is added over 70 minutes to a stirred slurry of diaminoguanidine hydrochloride (9.91 g, 0.079 mol) in 2B alcohol (60 mL) and water (15 mL) at 45° C. The resulting solution is refluxed for one hour, cooled to 5° C. and the hydrochloride salt collected by filtration and washed with cold alcohol and ether to give a white solid (40.5 g, 2 crops, 96%): mp 262°–264° C.

The hydrochloride salt (40.53 g, 0.076 mol) is stirred with ethyl acetate (250 mL) and neutralized with aqueous potassium carbonate (3.62 mol, 50 mL). The organic layer is washed with water, dried over Na₂SO₄, filtered and evaporated to a yellow solid. Crystallization from benzene-hexane gives the product as a yellow powder (37.4 g, 99%) with mp 125°–130° C.

EXAMPLE 3

Preparation of
1-amino-3-{[p-(trifluoromethyl)benzylidene]amino}-guanidine, hydrochloride and
p-tolualdehyde,α,α,α,-trifluoro-, oxime, (E)-

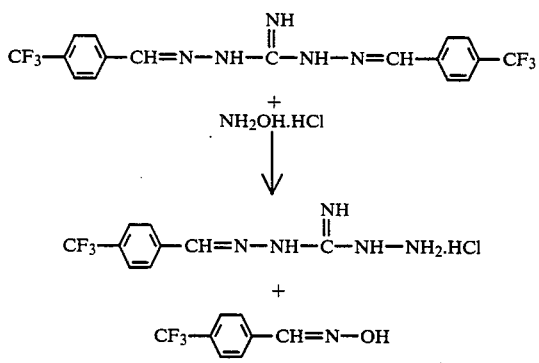

A mixture of 1,3-bis{[p-(trifluoromethyl)benzylidene]amino}guanidine (15.0 g, 0.0374 mol), hydroxylamine hydrochloride (2.76 g, 0.0393 mol) and ethanol (95%, 100 mL) is refluxed for one hour and 30 minutes. After stirring at room temperature for 16 hours, the reaction mixture is cooled in a freezer and the white solid is filtered (7.25 g). The filtrate is evaporated to approximately 30 mL and then cooled. The resulting purple solid (4.4 g) is collected by filtration and reslurried in hot chloroform (75 mL). Filtration gave the title hydrochloride as a white solid with mp 246°–249° C. (dec).

The filtrate is evaporated to approximately 10 mL and then cooled. The title oxime is collected by filtration as a white powder (1.72 g) mp 98°–102.5° C.

Using a similar procedure, 1-amino-3-p{[p-(1,1,2,2-tetrafluoroethoxy)benzylidene]amino}guanidine hydrochloride (white solid, mp 205°–212° C.); 1-amino-3-{p-(trifluoroethoxy)benzylidene]amino}guanidine hydrochloride (white powder; mp 235°–238° C.); and 1-amino-3-(p-chlorobenzylideneamino)guanidine hydrochloride may be prepared. The second products of the reactions, p-(1,1,2,2-tetrafluoroethoxy)benzaldehyde oxime (pinkish white solid, mp 47°–53.5° C.); α,α,α-trifluoro-p-anilaldehyde oxime (off-white solid, mp 46°–49.5° C.) and p-chlorbenzaldehyde oxime may also be isolated from the reactions.

EXAMPLE 4

Preparation of
1-{[p-(1,1,2,2-tetrafluoroethoxy)benzylidene]amino}-3-{[p-(trifluoromethyl)benzylidene]amino}guanidine

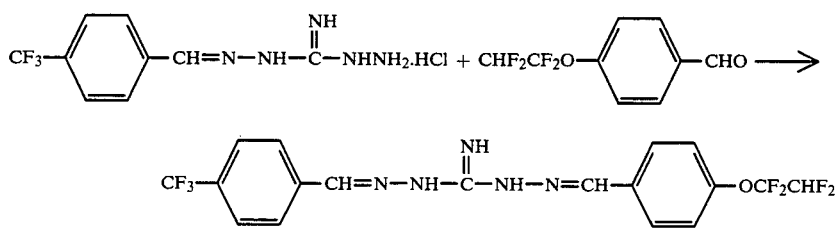

p-Tetrafluoroethoxybenzaldehyde (1.7 g) in 4 mL of ethanol is added over three minutes to a stirred and warm mixture of 2.0 g of 1-amino-3-{[p-(trifluoromethyl)benzylidene]amino}guanidine hydrochloride in 9 mL of 8:1 ethanol/water. After heating at reflux for one hour, the mixture is concentrated in vacuo to give 3.6 g of a white solid. The solids are dissolved in 150 mL of chloroform and treated with 10 mL of 3.6M potassium carbonate and 50 mL of water containing 5% sodium hydroxide. The product is extracted into ethyl acetate 300 mL and the organic layer washed with salt solution, dried over sodium sulfate and concentrated in vacuo to give 3.3 g of yellow solid. Crystallization from hexane-chloroform afforded 2.6 g of the title product as a yellow solid with mp 132°–137° C.

Utilizing the procedures of Examples 2 and 4 and substituting the appropriate aldehyde and guanidine yields compounds illustrated below.

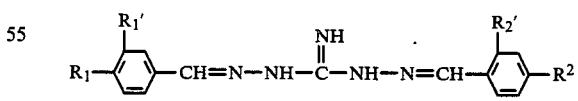

wherein unless specified $R_1'$ and $R_2'$ are H.

| | Free base or Salt | Physical appearance | mp °C. |
|---|---|---|---|
| Symmetrical diaminoguanidine hydrazones | | | |
| $R_1 = R_2$ | | | |
| 4-CF₃ | Free base | Yellow solid | 181–182 |
| 4-F | Free base | Pale yellow solid | 166–167 |
| 4-F | HCl salt | White solid | 289.5–290 |

-continued

| | Free base or Salt | Physical appearance | mp °C. |
|---|---|---|---|
| 4-HCF$_2$CF$_2$O | Free base | Pale yellow powder | 127–130.5 |
| 4-CF$_3$O | Free base | Yellow solid | 118–120 |
| 4-HCF$_2$O | Free base | Yellow solid | 132–135 |
| 4-HCF$_2$O | HCl salt | White solid | 235–235.5 |
| 4-HCCl$_2$CF$_2$O | Free base | Yellow solid | 90–92.5 |
| 4-HCCl$_2$CF$_2$O | HCl salt | White solid | 243–245 |
| 4-H–C(Cl)(F)–CF$_2$O | Free base | Yellow solid | 86–91 |
| 4-H–C(Cl)(F)–CF$_2$O | HCl salt | White solid | 241–247 |
| 4-HCF$_2$CF$_2$S | Free base | Yellow solid | 135–139 |
| 4-HCF$_2$CF$_2$S | HCl salt | Yellow white fluffy solid | 273–278 (dec) |
| 4-CF$_3$CH$_2$O | Free base | Light yellow powder | 160–162 |
| 4-CF$_3$CH$_2$O | HCl salt | Beige crystalline solid | 230–236 |
| 4-HCF$_2$S | Free base | Yellow solid | 141.5–143 |
| 4-HCF$_2$S | HCl Salt | White solid | 253–254 (dec) |

R$_1$R$_1$'/R$_2$R$_2$'

| | | | | |
|---|---|---|---|---|
| 3,4- CH$_3$ O—, CH$_3$ O— | | HCl salt | White powder | 243–247 |
| 3,4- F O—, F O— | | HCl salt | White powder | 301–305 |
| 3,4- H,F / F,F O—, O— | | Free base | Pale yellow solid | 132–135 |
| 3,4- H,F / F,F O—, O— | | HCl salt | White solid | 216–244 |

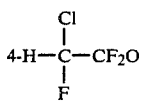

Unsymmetrical diaminoguanidine hydrazones

R$_1$ R$_2$

| | Free base or Salt | Physical appearance | mp °C. |
|---|---|---|---|
| CF$_3$ Cl | Free base | Yellow solid | 184–186 |
| CF$_3$ Br | Free base | Yellow solid | 187.5–188 |
| CF$_3$ Br | HI salt | Yellow solid | 243–244 |
| CF$_3$ HCF$_2$CF$_2$O | Free base | Yellow powder | 132–137 |
| Br HCF$_2$CF$_2$O | Free base | Yellow powder | 149–158 |
| Cl HCF$_2$CF$_2$O | Free base | Yellow solid | 177–180 |
| Cl HCF$_2$CF$_2$O | HCl salt | White solid | 251–259 |
| CF$_3$O HCF$_2$CF$_2$O | Free base | Yellow powder | 106–109 |
| CF$_3$O HCF$_2$CF$_2$O | HCl salt | White solid | 261–263.5 (dec) |

EXAMPLE 5

Preparation of 4,4-dimethyl-2-{[p-(1,1,2,2-tetrafluoroethoxy)benzylidene]amino}-allophanimidic acid [p-(1,1,2,2-tetrafluoroethoxy)benzylidene]hydrazide

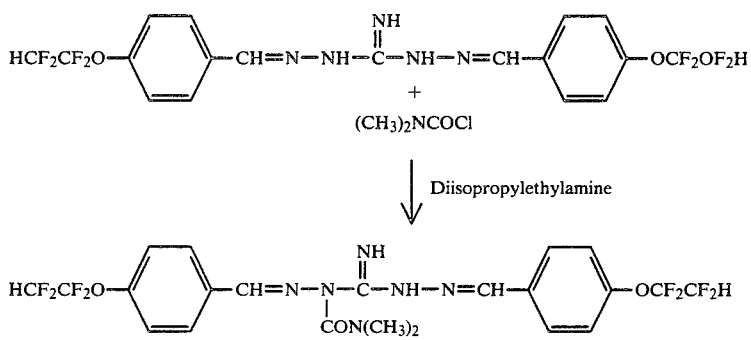

A solution of 1,3-bis{[p-(1,1,2,2-tetrafluoroethoxy)-benzylidene]amino}guanidine (29.84 g, 0.06 mol), diisopropylethylamine (15.51 g, 0.12 mol) and dimethylcarbamoyl chloride (129.2 g, 0.12 mol) in acetonitrile (200 mL) is stirred at reflux for 22 hours. The reaction mixture is cooled, and the acetonitrile is evaporated under reduced pressure. The residue is dissolved in ethyl acetate (250 mL), and the organic solution is washed with water, saturated NaCl and dried over Na$_2$SO$_4$. The solvent is evaporated under reduced pressure, and the residue is crystallized from benzene-hexanes to give the desired product as a yellow solid, mp 141.5°–143.5° C. in 92.9% yield.

Utilizing the above procedure and substituting the appropriate dialkylcarbamoyl chloride and diaminoguanidine hydrazone compound, yields the compounds illustrated below.

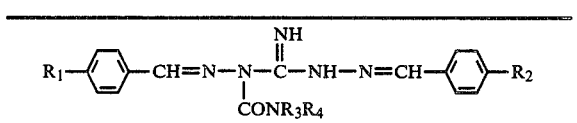

| R$_3$ | R$_4$ | R$_3$ | R$_4$ | mp °C. |
|---|---|---|---|---|
| CF$_3$ | CF$_3$ | CH$_3$ | CH$_3$ | 124–126 |
| Cl | Cl | CH$_3$ | CH$_3$ | 169–161 |
| Br | Br | CH$_3$ | CH$_3$ | 172–178 |
| CF$_3$O | CF$_3$O | CH$_3$ | CH$_3$ | 113–115 |
| HCF$_2$O | HCF$_2$O | CH$_3$ | CH$_3$ | 83.5–85.5 |
| HCCl$_2$CF$_2$O | HCCl$_2$CF$_2$O | CH$_3$ | CH$_3$ | 153–154 |
| HCFClCF$_2$O | HCFClCF$_2$O | CH$_3$ | CH$_3$ | 142–144 |
| HCF$_2$CF$_2$S | HCF$_2$CF$_2$S | CH$_3$ | CH$_3$ | 143–146 |
| F | F | CH$_3$ | CH$_3$ | 186–187 |
| HCF$_2$S | HCF$_2$S | CH$_3$ | CH$_3$ | 130–133 |
| {HCF$_2$CF$_2$O | {Br | CH$_3$ | CH$_3$ | 60–65 |

-continued

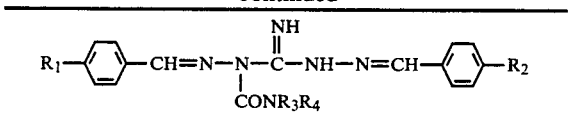

| $R_3$ | $R_4$ | $R_3$ | $R_4$ | mp °C. |
|---|---|---|---|---|
| and Br} | and HCF$_2$CF$_2$O} | — | — | |
| {CF$_3$ and Br} | {Br and CF$_3$} | CH$_3$ | CH$_3$ | 129–130 |
| {CF$_3$ and Cl} | {Cl and CF$_3$} | CH$_3$ | CH$_3$ | 149–151 |
| {CF$_3$O and HCF$_2$CF$_2$O} | {HCF$_2$CF$_2$O and CF$_3$O} | CH$_3$ | CH$_3$ | 102–120 |
| CF$_3$ | CF$_3$ | C$_2$H$_5$ | C$_2$H$_5$ | 150–151 |
| HCF$_2$CF$_2$O | HCF$_2$CF$_2$O | C$_2$H$_5$ | C$_2$H$_5$ | 99–100 |
| CF$_3$O | CF$_3$O | C$_2$H$_5$ | C$_2$H$_5$ | 67–70 |
| CF$_3$ | CF$_3$ | —(CH$_2$)$_4$— | | 120–123 |
| HCF$_2$CF$_2$O | HCF$_2$CF$_2$O | —(CH$_2$)$_4$— | | 136–137 |

EXAMPLE 6

Preparation of allophanimidic acid, 4-(2-chloroethyl)-2-{[p-(trifluoromethyl)benzylidene]amino}-allophanimidic acid [p-(trifluoromethyl)benzylidene]hydrazide

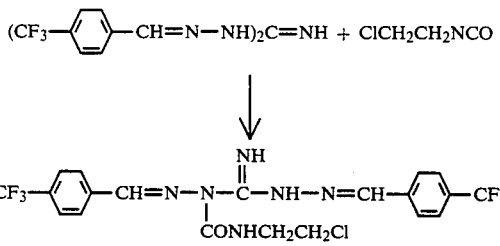

A solution of 2-chloroethylisocyanate (2.9 g, 0.0275 mol) in ether (8 mL) is slowly added to a slightly turbid mixture of 1,3-bis{[p-(trifluoromethyl)benzylidene]amino}guanidine (10.03 g, 0.025 mol) in ether (200 mL). After stirring for two hours at room temperature, the product is collected by filtration, washed with ether, and dried in a vacuum oven at 50°–60° C. to give 11.78 g of the above product with a mp 133° C.

Utilizing the above procedure and substituting the appropriate substituted or unsubstituted isocyanate and diaminoguanidine hydrazone compound yields the compounds illustrated below.

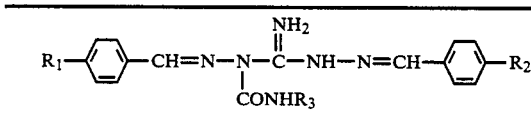

| $R_1$ | $R_2$ | $R_3$ | mp °C. |
|---|---|---|---|
| CF$_3$ | CF$_3$ | CH$_3$ | 146.5–147 |
| Cl | Cl | CH$_3$ | Decomposes on heating |
| HCF$_2$O | HCF$_2$O | CH$_3$ | 113.0–114 |
| HCF$_2$CF$_2$O | HCF$_2$CF$_2$O | CH$_3$ | 139.5–142.5 |
| CF$_3$ | CF$_3$ | C$_2$H$_5$ | 180 |
| HCF$_2$CF$_2$O | HCF$_2$CF$_2$O | C$_2$H$_5$ | 119.0–120.5 |
| HCF$_2$CF$_2$O | HCF$_2$CF$_2$O | ClCH$_2$CH$_2$ | 116.0–118 |

EXAMPLE 7

Preparation of 3-[p-(trifluoromethyl)benzylidene]-2-{{[p-(trifluoromethyl)benzylidene]amino}amidino}carbazate

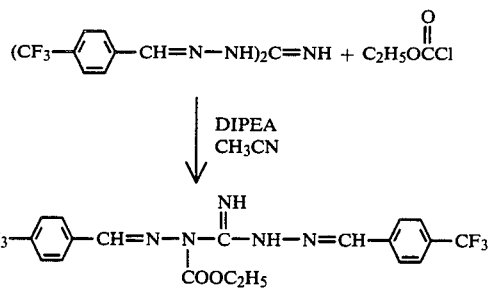

Ethyl chloroformate (2.98 g, 0.0275 mol) is added dropwise to a refluxing solution of 1,3-bis{[p-trifluoromethyl)benzylidene]amino}guanidine (10.03 g, 0.025 mol) and diisopropylethylamine DIPEA (3.55 g, 0.0275 mol) in acetonitrile (130 mL). After refluxing for one hour the mixture is cooled and acetonitrile (50 mL) is added. The resulting white solids collected by filtration, are washed with acetonitrile and dried in a vacuum oven at 50°–60° C. to give 6.9 g. The solid is slurried in hot isopropanol and filtered to give the product as white fluffy needles (6.0 g), mp 202° C.

EXAMPLE 8

Preparation of 2,2,2-trichloroethyl 3-[p-(trifluoromethyl)benzylidene]-2-{{[p-trifluoromethyl)benzylidene]amino}amidino}carbazate

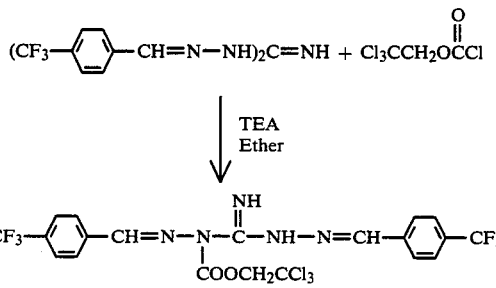

A solution of 2,2,2-trichloroethyl chlorformate (2.33 g, 0.011 mol) in ether (10 mL) is added dropwise to a solution of 1,3-bis{[p-(trifluoromethyl)benzylidene]amino}guanidine (4.01 g, 0.01 mol) and triethylamine (1.13 g, 0.011 mol) in ether (80 mL). The resulting mixture is stirred for one hour and then allowed to stand overnight. Additional 2,2,2-trichloroethyl chlorformate (2.33 g, 0.011 mol) and triethylamine 11.13 g, 0.011 mol) are added and stirring continued for four hours. The reaction mixture is filtered and the filtrate evaporated to dryness. The residue is dissolved in ethyl acetate, and the mixture is washed with water, dried over Na$_2$SO$_4$, filtered, and evaporated to a pale yellow solid. Successive crystallizations from toluene and isopropanol gave the title product (0.54 g) with mp 150.5°–151° C.

EXAMPLE 9

Preparation of 3-[p-(trifluoromethyl)benzylidene]-2-{{[p-(trifluoromethyl)benzylidene]amino}amidino}carbazate ester

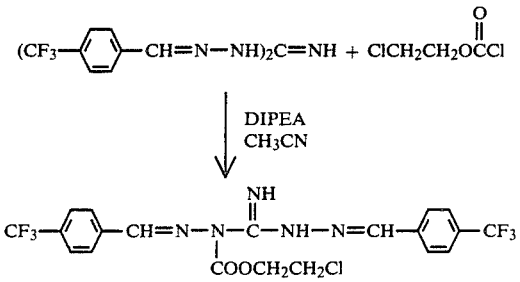

A solution of 2-chloroethyl chloroformate (235.9 g, 1.65 mol) in acetonitrile (250 mL) is added in a steady stream to a solution of 1,3-bis-{[p-(trifluoromethyl)benzylidene]amino}guanidine (602.0 g, 1.5 mol) and diisopropylethylamine (213.3 g, 1.65 mol) in acetonitrile (7500 mL) while the temperature is maintained below 35° C. Additional acetonitrile (1000 mL) is added and the reaction mixture stirred for one hour. The fluffy white solids are collected by filtration, washed with acetonitrile (2000 mL) and dried to give 610 g of the product with mp 188° C.

Utilizing the procedures of examples 7, 8, and 9 and substituting the appropriate hydrazone and chloroformate gives the compounds illustrated below.

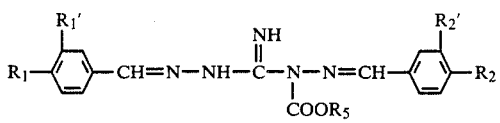

wherein unless specified $R_1'$ and $R_2'$ are H.

| $R_1$ | $R_2$ | $R_5$ | Physical appearance | mp °C. |
|---|---|---|---|---|
| $CF_3$ | $CF_3$ | $CH_3$ | White solid | 174–174.5 |
| $HCF_2CF_2O$ | $HCF_2CF_2O$ | $CH_3$ | White solid | 181–183 |
| Cl | Cl | $CH_3$ | White solid | 189.5–190 |
| $CF_3$ | $CF_3$ | $C_2H_5$ | White needles | 202 |
| Cl | Cl | $C_2H_5$ | White solid | 154–185 |
| $HCF_2O$ | $HCF_2O$ | $C_2H_5$ | Pale yellow solid | 154–155 |
| $HCF_2CF_2O$ | $HCF_2CF_2O$ | $C_2H_5$ | White solid | 152.5–155 |
| $CF_3O$ | $CF_3O$ | $C_2H_5$ | Cream color solid | 169–170 |
| $CF_3$ and Cl | Br and $CF_3$ | $C_2H_5$ | White solid | 189–189.5 |
| $HCF_2S$ | $HCF_2S$ | $C_2H_5$ | Pale yellow solid | 152–153 |
| $HCF_2O$ | $HCF_2O$ | $C_2H_5$ | Pale yellow solid | 134–135 |
| $CF_3$ | $CF_3$ | n-$C_3H_7$ | White solid | 181–182 |
| $CF_3$ | $CF_3$ | i-$C_3H_7$ | White solid | 178–178.5 |
| $HCF_2CF_2O$ | $HCF_2CF_2O$ | i-$C_3H_7$ | White solid | 129–131.5 |
| $HCCl_2CF_2O$ | $HCCl_2CF_2O$ | i-$C_3H_7$ | White solid | 131–133 |
| $CF_3O$ | $CF_3O$ | i-$C_3H_7$ | White solid | 142–144 |
| HC(F)(Cl)−$CF_2O$ | HC(F)(Cl)−$CF_2O$ | i-$C_3H_7$ | White powder | 127.5–130 |
| $HCF_2CF_2S$ | $HCF_2CF_2S$ | i-$C_3H_7$ | Pale yellow fluffy solid | 120–124 |
| $CF_3$ | $CF_3$ | n-$C_4H_9$ | White needles | 185 |
| $CF_3$ | $CF_3$ | i-$C_4H_9$ | White solid | 184–184.5 |
| $CF_3$ | $CF_3$ | sec-$C_4H_9$ | White solid | 153.5–154 |
| $CF_3O$ | $CF_3O$ | sec-$C_4H_9$ | White solid | 126–128.5 |
| Cl | Cl | sec-$C_4H_9$ | White solid | 149–150 |
| $CF_3$ | $CF_3$ | $CH_2CH_2Cl$ | White solid | 188 |
| $CF_3O$ | $CF_3O$ | $CH_2CH_2Cl$ | Fluffy white solid | 166–167 |
| $HCF_2CF_2O$ | $HCF_2CF_2O$ | $CH_2CH_2Cl$ | Pale orange-white solid, and remelt at | 128–135, 170–182 |
| {$HCF_2CF_2O$ and Cl} | {Cl and $HCF_2CF_2O$} | $CH_2CH_2Cl$ | Light brown- | 117–119 |
| HC(F)(Cl)−$CF_2O$ | HC(F)(Cl)−$CF_2O$ | $CH_2CH_2Cl$ | Off-white powder | 110–137 |
| {$HCF_3CF_2O$ and $CF_3O$} | {$CF_3O$ and $HCF_2CF_2O$} | $CH_2CH_2Cl$ | Off-white powder | 120–180 |
| $HCF_2S$ | $HCF_2S$ | $CH_2CH_2Cl$ | White solid | 138–139 |
| $CF_3$ | $CF_3$ | $CH_2CH_2Cl$ | Light beige powder | 155–160 |
| $CF_3$ | $CF_3$ | $CH_2CH_2Br$ | White solid | 184–185 |
| $CF_3$ | $CF_3$ | $CH_2CCl_3$ | Pale yellow solid | 150.5–151 |
| $CF_3O$ | $CF_3O$ | $CH_2CCl_3$ | Cream color solid | 137.5–140 |
| $CF_3$ | $CF_3$ | $C(CH_3)_2$−$CCl_3$ | Fluffy white solid | 162–164 |
| $CF_3$ | $CF_3$ | $CH_2$−CH=$CH_2$ | White solid | 190 |
| $HCCl_2$−$CF_2O$ | $HCCl_2$−$CF_2O$ | $CH_2$−CH− | White solid | 165–166 |
| $CF_3O$ | $CF_3O$ | $CH_2CH_2$−$CH_2$ | White solid | 176.5–177 |
| $CF_3$ | $CF_3$ | $CH_2$−CH($C_2H_5$)−$C_4H_9$-n | White solid | 146.5–147.5 |
| $CF_3$ | $CF_3$ | oleyl | White solid | 137–140 |
| $CF_3$ | $CF_3$ | $CH_2$−phenyl | White solid | 168–169 |

$R_1R_1'/R_2R_2'$

-continued

| $R_1$ | $R_2$ | $R_5$ | Physical appearance | mp °C. |
|---|---|---|---|---|
| 3,4-  | | $\underline{i}$-$C_3H_7$ | White solid | 125–132 |

EXAMPLE 10

The insecticidal activity of the compounds of this invention is demonstrated by the following tests wherein compounds are evaluated against test insect species at rates of from 10 to 1000 ppm. Test formulations and procedures used for evaluation are as follows:

Test Formulations

A. 100 mg of the test material is weighed, placed in a funnel over a 113 g narrow-mouth bottle, rinsed into the bottle with a 35 mL scoop of acetone, followed by a 35 mL scoop of water and another 35 mL scoop of acetone to yield 1000 ppm in 65% acetone. If the material is not soluble, it is broken up with a glass rod and used as a suspension.

B. This stock solution ("A") is used to make 300 ppm solutions or suspensions by pipetting 30 mL of "A" into a bottle containing 70 mL of 50% acetone to yield 300 ppm. Further dilutions in 50% acetone are made as required.

C. Tests requiring 10 ppm acetone solutions: 1 mL of "A" is pipetted into 99 mL of acetone to yield 10 ppm. Additional dilutions are made using 50% acetone as required.

Initial Tests

Tobacco Budworm—*Heliothis virescens* (Fabricus)

A cotton plant with two true leaves expanded is dipped for three seconds with agitation in 300 ppm solution. A 1.27 to 1.91 cm square of cheesecloth with about 50 to 100 budworm eggs 0–24 hours old is also dipped in the test solution and placed on a leaf of the cotton plant, all being placed in the hood to dry. The leaf with the treated budworm eggs is removed from the plant and placed in a 226 g Dixie cup with a wet 5 cm piece of dental wick and covered with a lid. The other leaf is placed in a similar cup with a wick and a piece of cheesecloth infested with 50–100 newly hatched larvae is added before covering the cup with a lid. After three days at 80° F., 50% relative humidity, observations of egg hatch are made, as well as kill of newly hatched larvae, any inhibition of feeding, or interference of any sort with normal development.

Southern Armyworm—*Spodoptera eridania* (Cramer)

A Sieva lima bean plant with just the primary leaves expanded to 1.91 cm is dipped for three seconds with agitation in the "A" solution of 1000 ppm and set in the hood to dry. Following this, one leaf is placed in a 9 cm petri dish which has a moist filter paper in the bottom and 10 third-instar armyworm larvae about 1 cm long. This dish is covered and held at 80° F., and 50% r.h. After two days, mortality counts and estimates of the amount of feeding are made. Compounds showing partial kill and/or inhibition of feeding are held for an extra day for further observations. Those materials which produce greater than 75% mortality, or which show only trace feeding damage are further tested.

All compounds showing activity as defined above are retested, using the second leaf on the bean plant, after an interval of seven days from original treatment, as an assay of residual activity.

Secondary Tests

Tobacco Budworm—*Heliothis virescens* (Fabricus)

Third Instar

Three cotton plants with just expanded cotyledons are dipped in 1000 ppm solution and placed in the hood to dry. When dry, each cotyledon is cut in half, and 10 are each placed in a 28 g plastic medicine cup containing a 1.25 cm dental wick saturated with water, and one third-instar budworm larva is added. The cup is capped and held for three days at 80° F., 50% relative humidity, after which mortality counts are made. Compounds killing more than 75% of the larvae are further tested.

| Rating System | |
|---|---|
| 0 | No effect |
| 1 | 11–25% |
| 2 | 26–35% |
| 3 | 36–45% |
| 4 | 46–55% |
| 5 | 56–65% |
| 6 | 66–75% |
| 7 | 76–85% |
| 8 | 86–99% |
| 9 | 100% |

Data obtained are reported in Table IA, IB and IC below.

TABLE IA

Evaluation of Diaminoguanidine Hydrazone Urea Compounds as Insecticides

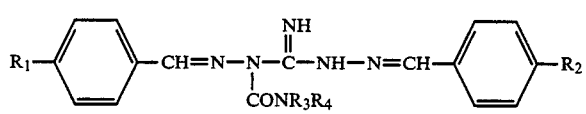

| Compound | | | | Mortality Rating | | | | | | | | | $LC_{50}/$ ppm Southern Armyworm | *$FD_{50}/$ ppm Southern Armyworm | $LC_{50}/$ ppm Tobacco Budworm | *$FD_{50}/$ ppm Tobacco Budworm |
|---|---|---|---|---|---|---|---|---|---|---|---|---|---|---|---|---|
| | | | | Southern Armyworm | | | Tobacco Budworm | | | | | | | | | |
| | | | | | | | 1st Instar | | | 3rd Instar | | | | | | |
| $R_1$ | $R_2$ | $R_3$ | $R_4$ | 1000 | 100 | 10 | 300 | 100 | 10 | 1000 | 100 | 10 | | | | |
| $CF_3$ | $CF_3$ | $CH_3$ | $CH_3$ | 9 | 9 | 8 | 8 | 6 | 0 | 9 | 9 | 0 | 15 | 12 | 96 | 3 |
| $HCF_2CF_2O$ | $HCF_2CF_2O$ | $CH_3$ | $CH_3$ | 9 | 9 | 0 | 9 | 5 | — | 8 | 2 | | 7, 7 | 8, 6 | 491 | 2, 5 |
| Cl | Cl | $CH_3$ | $CH_3$ | 9 | 0 | — | 0 | — | — | 0 | 0 | — | — | — | — | — |
| Br | Br | $CH_3$ | $CH_3$ | 9 | 9 | 0 | 0 | — | — | 2 | 0 | — | — | — | — | — |

TABLE IA-continued
Evaluation of Diaminoguanidine Hydrazone Urea Compounds as Insecticides $$R_1-\text{C}_6H_4-CH=N-N(CONR_3R_4)-C(=NH)-NH-N=CH-C_6H_4-R_2$$

| Compound | | | | Mortality Rating | | | | | | | | | $LC_{50}$/ppm Southern Army-worm | *$FD_{50}$/ppm Southern Army-worm | $LC_{50}$/ppm Tobacco Bud-worm | *$FD_{50}$/ppm Tobacco Bud-worm |
|---|---|---|---|---|---|---|---|---|---|---|---|---|---|---|---|---|
| | | | | Southern Armyworm | | | Tobacco Budworm | | | | | | | | | |
| | | | | | | | 1st Instar | | | 3rd Instar | | | | | | |
| $R_1$ | $R_2$ | $R_3$ | $R_4$ | 1000 | 100 | 10 | 300 | 100 | 10 | 1000 | 100 | 10 | | | | |
| $CF_3O$ | $CF_3O$ | $CH_3$ | $CH_3$ | 9 | 9 | 9 | — | — | — | 9 | 3 | — | 10, 23 | 8, 30 | 77, 72 | 1, 4 |
| $HCF_2O$ | $HCF_2O$ | $CH_3$ | $CH_3$ | 9 | 9 | 0 | 0 | — | — | 0 | — | — | 75 | 46 | — | — |
| $HCCl_2CF_2O$ | $HCCl_2CF_2O$ | $CH_3$ | $CH_3$ | 9 | 9 | — | — | — | — | 0 | 2 | — | 26 | 28 | 140 | <30 |
| $HC(Cl)(F)-CF_2O$ | $HC(Cl)(F)-CF_2O$ | $CH_3$ | $CH_3$ | 9 | 9 | 9 | — | — | — | 9 | 4 | 0 | — | — | 201 | 10 |
| $HCF_2CF_2S$ | $HCF_2CF_2S$ | $CH_3$ | $CH_3$ | 9 | 9 | 3 | — | — | — | 6 | 6 | 0 | — | — | — | — |
| F | F | $CH_3$ | $CH_3$ | 8 | 0 | — | — | — | — | 0 | — | — | — | — | — | — |
| $HCF_2S$ | $HCF_2S$ | $CH_3$ | $CH_3$ | 9 | 9 | 0 | — | — | — | 0 | — | — | — | — | — | — |
| $HCF_2CF_2O$ and BR | Br and $HCF_2CF_2O$ | $CH_3$ | $CH_3$ | 9 | 9 | 9 | — | — | — | 6 | 0 | — | — | — | — | — |
| $CF_3$ and Br | Br and $CF_3$ | $CH_3$ | $CH_3$ | 0 | 9 | 0 | — | — | — | 6 | 0 | — | — | — | — | — |
| $CF_3$ and Cl | Cl and $CF_3$ | $CH_3$ | $CH_3$ | 9 | 9 | 5 | — | — | — | 0 | 0 | — | — | — | — | — |
| $CF_3O$ and $HCF_2CF_2O$ | $HCF_2CF_2O$ and $CF_3O$ | $CH_3$ | $CH_3$ | 9 | 9 | — | — | — | — | 7 | 3 | — | — | — | — | — |
| $CF_3$ | $CF_3$ | $CH_3$ | H | 9 | 9 | 1 | 8 | 0 | — | 6 | — | — | 5 | 5 | — | — |
| $HCF_2O$ | $HCF_2O$ | $CH_3$ | H | 9 | 0 | — | 7 | — | — | 0 | — | — | — | — | — | — |
| $HCF_2CF_2O$ | $HCF_2CF_2O$ | $CH_3$ | H | 9 | 9 | 0 | — | — | — | 4 | — | — | 16, 34 | 12, 19 | — | — |
| $CF_3$ | $CF_3$ | $C_2H_5$ | $C_2H_5$ | 9 | 9 | 7 | 0 | — | — | 4 | — | — | 8, 12 | 8, 11 | — | — |
| $HCF_2CF_2O$ | $HCF_2CF_2O$ | $C_2H_5$ | $C_2H_5$ | 9 | 9 | 1 | — | — | — | 5 | 0 | 0 | — | — | — | — |
| $CF_3O$ | $CF_3O$ | $C_2H_5$ | $C_2H_5$ | 9 | 9 | 0 | — | — | — | 8 | — | — | — | — | — | — |
| $CF_3$ | $CF_3$ | $C_2H_5$ | H | 9 | 0 | — | 0 | — | — | 0 | — | — | — | — | — | — |
| $HCF_2CF_2O$ | $HCF_2CF_2O$ | $C_2H_5$ | H | 9 | 9 | 0 | — | — | — | 4 | — | — | 34 | 12 | — | — |
| $CF_3$ | $CF_3$ | $-(CH_2)_4-$ | | 9 | 9 | 9 | — | — | — | 9 | 4 | 0 | 18, 14 | 14, 12 | 1000 | 30 |
| $HCF_2CF_2O$ | $HCF_2CF_2O$ | $-(CH_2)_4-$ | | 9 | 9 | — | — | — | — | 3 | 0 | — | — | — | — | — |
| $CF_3$ | $CF_3$ | $ClCH_2CH_2$ | H | 9 | 9 | — | 0 | — | — | 9 | 4 | — | 11, 37 | 10, 12 | 654 | 13 |
| $HCF_2CF_2O$ | $HCF_2CF_2O$ | $ClCH_2CH_2$ | H | 9 | 8 | 0 | — | — | — | 6 | 0 | 0 | 21 | 17 | — | — |

$FD_{50}$ = The concentration of insecticide required to reduce insect feeding by 50%.

TABLE IB
Diaminoguanidine hydrazones as insecticides

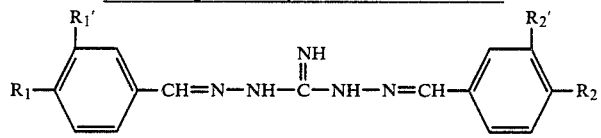

wherein unless specified $R_1'$ and $R_2'$ are H

| Compound | | Free Base, B or salt, S | Mortality Rating | | | | | | | | |
|---|---|---|---|---|---|---|---|---|---|---|---|
| | | | Southern Armyworm | | | Tobacco Budworm | | | | | |
| | | | | | | 1st Instar | | | 3rd Instar | | |
| $R_1$ | $R_2$ | | 1000 | 100 | 10 | 300 | 100 | 10 | 1000 | 100 | 10 |
| | $CF_3$ | B | 9 | 9 | 0 | 6 | 0 | — | 8 | 0 | — |
| | F | B | 9/R* | 2 | — | 0 | 0 | — | 3 | — | — |
| | F | S | 9 | 2 | — | — | — | — | — | — | — |
| | $HCF_2CF_2O$ | B | 9 | 9 | 0 | 9 | 0/R | — | 9 | 0 | — |
| | $CF_3O$ | B | 9 | 9 | 4 | — | — | — | 7 | — | — |
| | $HCF_2O$ | B | 9 | 6 | 0 | 0 | — | — | 0 | — | — |
| | $HCF_2O$ | S | 9 | 8 | 0 | 0 | — | — | 0 | — | — |
| | $HCCl_2CF_2O$ | B | 9 | 0 | 0 | — | — | — | 4/R | — | — |
| | $HCCL_2CF_2O$ | S | 9 | 9 | 7 | — | — | — | 5 | 0/R | — |
| | $HC(Cl)(F)-CF_2O$ | B | 9 | 9 | 7 | — | — | — | 9 | 0 | 0 |
| | | | | | 0 | | | | | | |

TABLE IB-continued

Diaminoguanidine hydrazones as insecticides

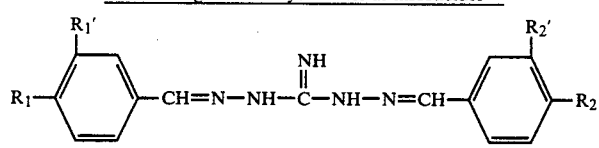

wherein unless specified $R_1'$ and $R_2'$ are H

| Compound | | Free Base, B or salt, S | Southern Armyworm | | | Tobacco Budworm | | | | | |
|---|---|---|---|---|---|---|---|---|---|---|---|
| | | | | | | 1st Instar | | | 3rd Instar | | |
| $R_1$ | $R_2$ | | 1000 | 100 | 10 | 300 | 100 | 10 | 1000 | 100 | 10 |
| | Cl / HC—CF$_2$O / F | S | 9 | 9 | 6 | — | — | — | 9/R | 0/R | 0/R |
| | HCF$_2$CF$_2$S | B | 9 | 9 | — | — | — | — | 0/R | — | — |
| | HCF$_2$CF$_2$S | S | 9 | 9 | 6 | — | — | — | 0/R | — | — |
| | CF$_3$CH$_2$O | B | 4 | 0 | — | — | — | — | 0/R | 0 | — |
| | CF$_3$CH$_2$ | S | 9 | 8 | 6 | — | — | — | 0/R | 0 | — |
| | HCF$_2$S | B | 8 | 9 | — | — | — | — | 0/R | 0/R | 0 |
| | HCF$_2$S | S | 9 | 9 | — | — | — | — | 0/R | — | — |
| CF$_3$ | Cl | B | 9 | 9 | — | — | — | — | 4/R | 0/R | 0 |
| CF$_3$ | Br | B | 9 | 9 | 9 | — | — | — | 0/R | — | — |
| CF$_3$ | Br | S | 9 | 8 | 0 | — | — | — | 0/R | 0/R | — |
| | | | | 9 | | | | | | | |
| CF$_3$ | HCF$_2$CF$_2$O | B | 9 | 9 | 9 | — | — | — | 3 | — | — |
| | | | | | 0 | | | | | | |
| Br | HCF$_2$CF$_2$O | B | 9 | 9 | — | — | — | — | 0/R | — | — |
| Cl | HCF$_2$CF$_2$O | B | 9 | 9 | 0 | — | — | — | 0/R | 0 | — |
| Cl | HCF$_2$CF$_2$O | S | 9 | 9 | — | — | — | — | 0/R | — | — |
| | | | 0 | 0 | | | | | | | |
| $R_1R_1'/R_2R_2'$ | | | | | | | | | | | |
| 3,4- CH$_3$ O— / CH$_3$ O— | | S | 9 | 8 9 | 6 | — | — | — | 0/R | 0 | — |
| 3,4- F O— / F O— | | S | 9 | 0 | 4 | — | — | — | 0/R | 0/R | — |
| 3,4- F—O— / F—O— / F | | B | 9 | 9 0 | 0 | — | — | — | 0/R | 0/R | — |
| 3,4- F—O— / F—O— / F | | S | 9 | 0 | — | — | — | — | 0/R | — | — |
| | Cl | HNO$_3$ | 9 | 0 | — | — | — | — | 0 | — | — |
| | Br | HNO$_3$ | 9 | 5 | — | 0 | — | — | — | — | — |
| | CF$_3$ | HCl | 9 | 9 | 0 | 9 | 0/R | 0 | 5 | 0/R | — |
| | Cl | HCl | 8 9/R | 0/R | 0 | — | — | — | 0 | — | — |
| | Cl | Base | 9 | 0 | 0 | 5 | — | — | 0 | — | — |
| | CF$_3$O | HCl | 9 | 9 | 0 | 9 | — | — | — | — | — |
| Cl | Br | HCl | 9 | 2/R | — | 0 | — | — | 0 | — | — |
| CF$_3$ | Br | HCl | 9 | — | — | 9 | 0/R | 0 | 0/R | 0/R | 0 |

R* - Indicates reduced feeding is observed

TABLE IC

Evaluation of diaminoguanidine hydrazones as insecticides

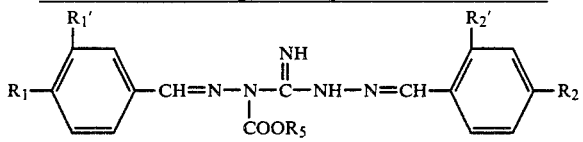

wherein unless specified $R_1'$ and $R_2'$ are H

| Compound | | | Mortality Rating | | | | | | | | |
|---|---|---|---|---|---|---|---|---|---|---|---|
| | | | Southern Armyworm | | | Tobacco Budworm | | | | | |
| | | | | | | 1st Instar | | | 3rd Instar | | |
| $R_1$ | $R_2$ | $R_5$ | 1000 | 100 | 10 | 300 | 100 | 10 | 1000 | 100 | 10 |
| $CF_3$ | $CF_3$ | $CH_3$ | 9 | 9 | 3 | — | — | — | 6/R* | — | — |
| $HCF_2CF_2O$ | $HCF_2CF_2O$ | $CH_3$ | 9 | 9 | 9 | — | — | — | — | — | — |
| $CF_3$ | $CF_3$ | $C_2H_5$ | 9 | 7 | 9 | — | — | — | — | — | — |
| Cl | Cl | $C_2H_5$ | 8 | 9 | — | — | — | — | — | — | — |
| $HCF_2O$ | $HCF_2O$ | $C_2H_5$ | 9 | 9 | 0 | — | — | — | 2 | — | — |
| $CF_3O$ | $CF_3O$ | $C_2H_5$ | 9 | 9 | 6 | — | — | — | 7/R | 2 | — |
| $CF_3$ and Br | Br and $CF_3$ | $C_2H_5$ | 9 | 9 | 0 | — | — | — | 0/R | — | — |
| $CF_3$ and Cl | Cl and $CF_3$ | $C_2H_5$ | 9 | 9 | 0 | — | — | — | 8 | 0/R | — |
| $HCF_2S$ | $HCF_2S$ | $C_2H_5$ | 9 | 0 | — | — | — | — | 0/R | — | — |
| $HCF_2S$ | $HCF_2O$ | $n$-$C_3H_7$ | 9 | 0 | — | — | — | — | 0 | — | — |
| $CF_3$ | $CF_3$ | $n$-$C_3H_7$ | 9 | 9 | 4 | — | — | — | 0 | — | — |
| $CF_3$ | $CF_3$ | $i$-$C_3H_7$ | 9 | 9 | 9 | 0 | — | — | 3/R | 0/R | — |
| $HCF_2CF_2O$ | $HCF_2CF_2O$ | $i$-$C_3H_7$ | 9 | 9 | 0 | — | — | — | 5 | 0 | — |
| $HCCL_2CF_2O$ | $HCCl_2CF_2O$ | $i$-$C_3H_7$ | 7 | 0 | — | — | — | — | 0/R | 0/R | — |
| $CF_3O$ | $CF_3O$ | $i$-$C_3H_7$ | 9 | 9 | 7 | — | — | — | 5 9 | 5/R | — |
| H—C(Cl)(F)—$CF_2O$ | H—C(Cl)(F)—$CF_2O$ | $i$-$C_3H_7$ | 9 | 9 | 0 | — | — | — | 0/R | — | — |
| $HCF_2CF_2S$ | $HCF_2CF_2S$ | $i$-$C_3H_7$ | 9 | 9 | — | — | — | — | 5/R | 0 | — |
| 3,4- F,F,F-O- (R_1R_1'/R_2R_2') | 3,4- F,F,F-O- | $i$-$C_3H_7$ | 8 | 5 | 0 | — | — | — | 0/R | 0 | — |
| $CF_3$ | $CF_3$ | $n$-$C_4H_9$ | 9 | 0 | — | — | — | — | 0 | — | — |
| $CF_3$ | $CF_3$ | $i$-$C_4H_9$ | 9 | 0 | — | 0 | — | — | 0 | — | — |
| $CF_3$ | $CF_3$ | sec-$C_4H_9$ | 9 | 9 | 6 | — | — | — | 6/R | 0/R | — |
| $CF_3O$ | $CF_3O$ | sec-$C_4H_9$ | 9 | 9 | 0 | — | — | — | 8 | 0/R | — |
| Cl | Cl | sec-$C_4H_9$ | 9 | 0 | — | — | — | — | 0/R | — | — |
| $CF_3$ | $CF_3$ | $ClCH_2CH_2$ | 9 | 9 | 8 | — | — | — | 2/R | 0 | — |
| $CF_3O$ | $CF_3O$ | $ClCH_2CH_2$ | 9 | 9 | 5 | — | — | — | 8/R | 0/R | 0/R |
| $HCF_2CF_2O$ and Cl | Cl and $HCF_3CF_2O$ | $ClCH_2CH_2$ | 9 | 9 | — | — | — | — | 0/R | — | — |
| HC(Cl)(F)—$CF_2O$ | HC(Cl)(F)—$CF_2O$ | $ClCH_2CH_2$ | 9 | 9 | — | — | — | — | 0/R | — | — |
| $HCF_2CF_2O$ and $CF_3O$ | $CF_3O$ and $HCF_2CF_2O$ | $ClCH_2$—$CH_2$ | 9 | 9 | — | — | — | — | 0/R | — | — |
| $HCF_2S$ | $HCF_2S$ | $ClCH_2CH_2$ | 9 | 0 | — | — | — | — | 0/R | — | — |
| $CF_3$ | $CF_3$ | $BrCH_2CH_2$ | 9 | 0 | 0 | — | — | — | 0 | — | — |
| $CF_3$ | $CF_3$ | $Cl_3CCH_2$ | 9 | 9 | 8 | — | — | — | 8 | 0/R | 0 |
| $CF_3O$ | $CF_3O$ | $Cl_3CCH_2$ | 9 | 9 | 9 | — | — | — | 0/R | 1/R | — |
| $CF_3$ | $CF_3$ | $Cl_3CC(CH_3)_2$ | 9 | 9 | 0 | — | — | — | 9 | 0/R | 0 |
| $CF_3$ | $CF_3$ | $CH_2=CH—CH_2$ | 9 | 9 | 0 | — | — | — | 0/R | 0 | — |
| $CF_3O$ | $CF_3O$ | $CH_2=CH—CH_2$ | 9 | 8 | 6 | — | — | — | 0/R | — | — |
| $CF_3$ | $CF_3$ | (phenyl)—$CH_2$ | 9 | 0 | — | 0 | — | — | 0 | — | — |

R* - indicates reduced feeding is observed

What is claimed is:

1. A compound of the formula

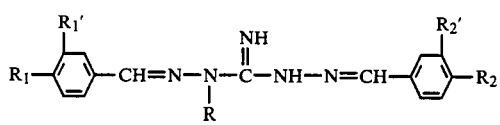

wherein $R_1'$ and $R_2'$ are H, and $R_1$ and $R_2$ are individually selected from fluoro, chloro, bromo, trifluoromethyl, $CF_3CH_2O$, $CHF_2X$, $CF_3X$, $CHY_2CF_2X$, or $CHFYCF_2X$, where X is O or S and Y is F or Cl; or wherein $R_1$ and $R_1'$ or $R_2$ and $R_2'$ are $-OCF_2O-$, $OCF_2CHFO-$, $OC(CH_3)_2-O-$, or $-OCF_2CF_2O-$;

R is

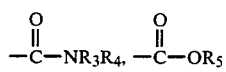

where $R_3$ is $C_1-C_2$ alkyl, or $C_1-C_2$ haloalkyl, $R_4$ is hydrogen or $C_1-C_2$ alkyl; or $R_3$ and $R_4$ when taken together may form a ring represented by $CH_2(CH_2)_n-$ where n is 3 or 4; $R_5$ is $C_1-C_4$ alkyl optionally substituted with one to three halogens or $C_3-C_4$ alkenyl, with the proviso that when R is

$R_1$ and $R_2$ are $CF_3CH_2O$, $CHF_2X$, $CF_3X$, $CHY_2CF_2X$, or $CHFYCF_2S$, where X is O or S and Y is F or Cl; $R_1$ and $R_1'$ or $R_2$ and $R_2'$ are $-OCF_2O-$; $OC(CH_3)_2-O-$, $OCF_2CHFO$ or $-OCF_2CF_2O-$.

2. The compound according to claim 1, 4,4-dimethyl-2-{[p-(trifluoromethyl)benzylidene]amino}allophanimidic acid, [p-(trifluoromethyl)benzylidene]hydrazide.

3. The compound according to claim 1, 4,4-dimethyl-2-{[p-(1,1,2,2-tetrafluoroethoxy)benzylidene]amino}-allophanimidic acid, [p-(1,1,2,2-tetrafluoroethoxy)benzylidene]hydrazide.

4. The compound according to claim 1, 4,4-dimethyl-2-{[p-(trifluoromethoxy)benzylidene]amino}-allophanimidic acid, [p-(trifluoromethoxy)benzylidene]hydrazide.

5. The compound according to claim 1, 4,4-diethyl-2-{[p-(trifluoromethyl)benzylidene]amino}-allophanimidic acid, [p-(trifluoromethyl)benzylidene]hydrazide.

6. The compound according to claim 1, 4-(2-chloroethyl)-2-{[p-trifluoromethyl)benzylidene]amino}-allophanimidic acid, [p-trifluoromethyl)benzylidene]hydrazide.

7. The compound according to claim 1, 3-[p-(trifluoromethoxy)benzylidene]-2-{{[p-trifluoromethoxy)-benzylidene]amino}amidino}-carbazic acid, 2-chloroethyl ester.

* * * * *